(12) United States Patent
Jamali

(10) Patent No.: US 8,187,336 B2
(45) Date of Patent: May 29, 2012

(54) DEVICE AND METHOD FOR RECONSTRUCTION OF OSSEOUS SKELETAL DEFECTS

(76) Inventor: Amir A. Jamali, Sacramento, CA (US)

(*) Notice: Subject to any disclaimer, the term of this patent is extended or adjusted under 35 U.S.C. 154(b) by 366 days.

(21) Appl. No.: 12/626,505

(22) Filed: Nov. 25, 2009

(65) Prior Publication Data

US 2010/0076572 A1    Mar. 25, 2010

Related U.S. Application Data

(63) Continuation-in-part of application No. 10/867,748, filed on Jun. 16, 2004, now abandoned.

(60) Provisional application No. 60/478,465, filed on Jun. 16, 2003.

(51) Int. Cl.
*A61F 2/28* (2006.01)
*A61F 2/30* (2006.01)

(52) U.S. Cl. ............... 623/23.52; 623/23.46; 623/23.54; 623/23.76

(58) Field of Classification Search .................. None
See application file for complete search history.

(56) References Cited

U.S. PATENT DOCUMENTS

| | | |
|---|---|---|
| 3,686,922 A | 8/1972 | Bley |
| 3,741,706 A | 6/1973 | Conley |
| 4,813,960 A | 3/1989 | Muller |
| 4,904,265 A | 2/1990 | MacCollum |
| 5,080,674 A | 1/1992 | Jacobs et al. |
| 5,176,711 A | 1/1993 | Grimes |
| 5,320,626 A | 6/1994 | Schmieding |
| 5,329,846 A | 7/1994 | Bonutti |
| 5,423,823 A | 6/1995 | Schmieding |
| 5,713,374 A | 2/1998 | Pachence |
| 5,782,835 A | 7/1998 | Hart |

(Continued)

FOREIGN PATENT DOCUMENTS

EP    346294    12/1989

(Continued)

OTHER PUBLICATIONS

Emmerson, B. C., et al. "Fresh Osteochondral Allografting in the Treatment of Osteochondritis Dissecans of the Femoral Condyle." American Journal of Sports Medicine 35.6 (2007): 907-14.

(Continued)

*Primary Examiner* — David H Willse
*Assistant Examiner* — Javier Blanco
(74) *Attorney, Agent, or Firm* — Craig M. Stainbrook; Stainbrook & Stainbrook, LLP

(57) ABSTRACT

A synovial joint implantable apparatus for the reconstruction of skeletal defects with a flexible member, which is preferably resorbable, attached to a rigid structural prosthesis such as a total hip or total knee replacement implant. The cavitary space defined and surrounded by the flexible member is filled with osteoconductive and/or inductive materials which eventually matures into new column of bone. The prosthesis is supported by the bed of graft material surrounding it and is gradually unloaded as the bed matures into solid bone. The fixation of the prosthesis into native bone depends on the specific implant and the anatomic area of its use. The flexible member is secured to the margins of the prosthesis using rails, runners, sutures, or other attachment devices that prevent the escape of the bone graft and maintain an initial column of support for the implant. Should the metal implant even need removal, the reconstituted bone can be separated from the implant in such a way as to restore bone stock and facilitate future revision surgical procedures.

9 Claims, 15 Drawing Sheets

U.S. PATENT DOCUMENTS

| | | | |
|---|---|---|---|
| 5,824,078 | A | 10/1998 | Nelson |
| 5,919,196 | A | 7/1999 | Bobic et al. |
| 6,132,470 | A | 10/2000 | Berman |
| 6,156,069 | A | 12/2000 | Amstutz |
| 6,214,049 | B1 | 4/2001 | Gayer et al. |
| 6,328,765 | B1 | 12/2001 | Hardwick et al. |
| 6,358,253 | B1 | 3/2002 | Torrie |
| 6,432,141 | B1 | 8/2002 | Stocks et al. |
| 6,458,161 | B1 | 10/2002 | Gibbs |
| 6,488,033 | B1 | 12/2002 | Cerundolo |
| 6,591,581 | B2 | 7/2003 | Schmieding |
| 6,595,999 | B2 | 7/2003 | Marchione |
| 6,989,034 | B2 | 1/2006 | Hammer et al. |
| 7,160,305 | B2 | 1/2007 | Schmieding |
| 7,241,315 | B2 | 7/2007 | Evans |
| 7,264,634 | B2 | 9/2007 | Schmieding |
| 2003/0130741 | A1 | 7/2003 | McMinn |
| 2003/0187514 | A1 | 10/2003 | McMinn |
| 2007/0135918 | A1 | 6/2007 | Malinin |
| 2007/0162038 | A1 | 7/2007 | Tuke |

FOREIGN PATENT DOCUMENTS

| | | |
|---|---|---|
| EP | 466638 | 1/1992 |
| FR | 2 315 902 | 1/1997 |
| WO | WO 9007308 | 7/1990 |
| WO | WO 9103993 | 4/1991 |

OTHER PUBLICATIONS

Jamali, A. A., et al. "Fresh Osteocondral Allografts: Results in the Patellofemoral Joint." Clin Orthop Relat Res. 437 (2005): 176-85.

Jamali, A. A.; Hatcher, S. L.; and You, Z. "Donor Cell Survival in a Fresh osteochondral Allograft at Twenty-Nine Years. A Case Report." J Bone Joint Surg Am 89.1 (2007): 166-9.

Lexer, E. "Substitution of Whole or Half Joints from Freshly Amputated Extremities by Free-Plastic Operation." Surg Gynecol. Obstet. 6 (1908): 601-07.

Meyers, M. H. "Resurfacing of the Femoral Head with Fresh Osteochondral Allografts. Long-Term Results." Clin Orthop. 197 (1985: 111-4.

Allograft OATS surgical technique, Arthrex, 1983.

McMinn, Derek. "Smith & Nephew Birmingham Hip Resurfacing Surgical Technique"; booklet dated Apr. 2006, Smith & Nephew, Memphis, TN, USA, 36 pgs.

Gortz, S. and Bugbee, W. D. "Allografts in Articular Cartilage Repair". J Bone Joint Surg Am 88.1 (2006): 1374-1384.

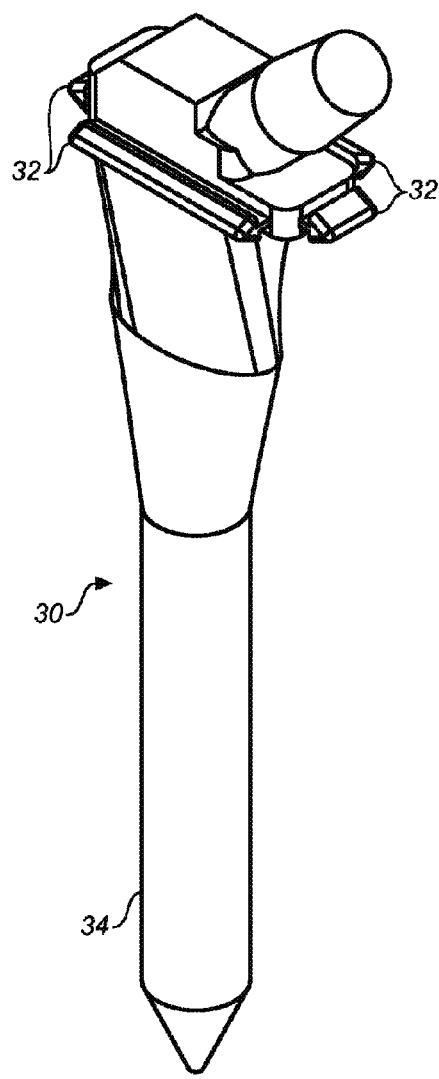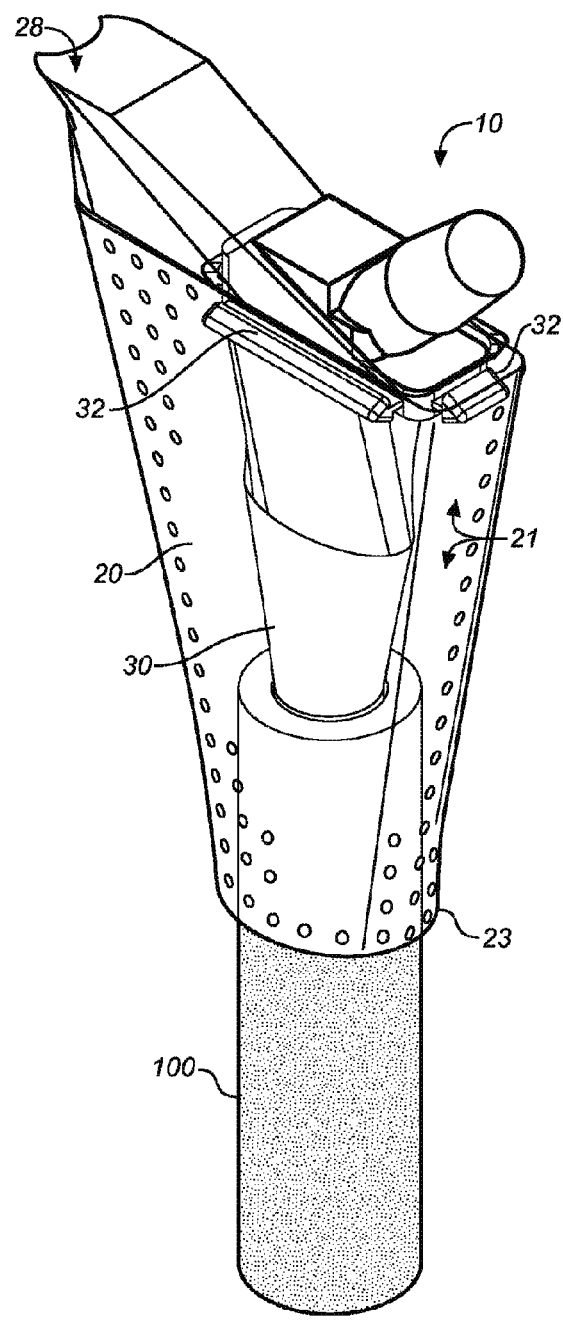
FIG. 2          FIG. 3

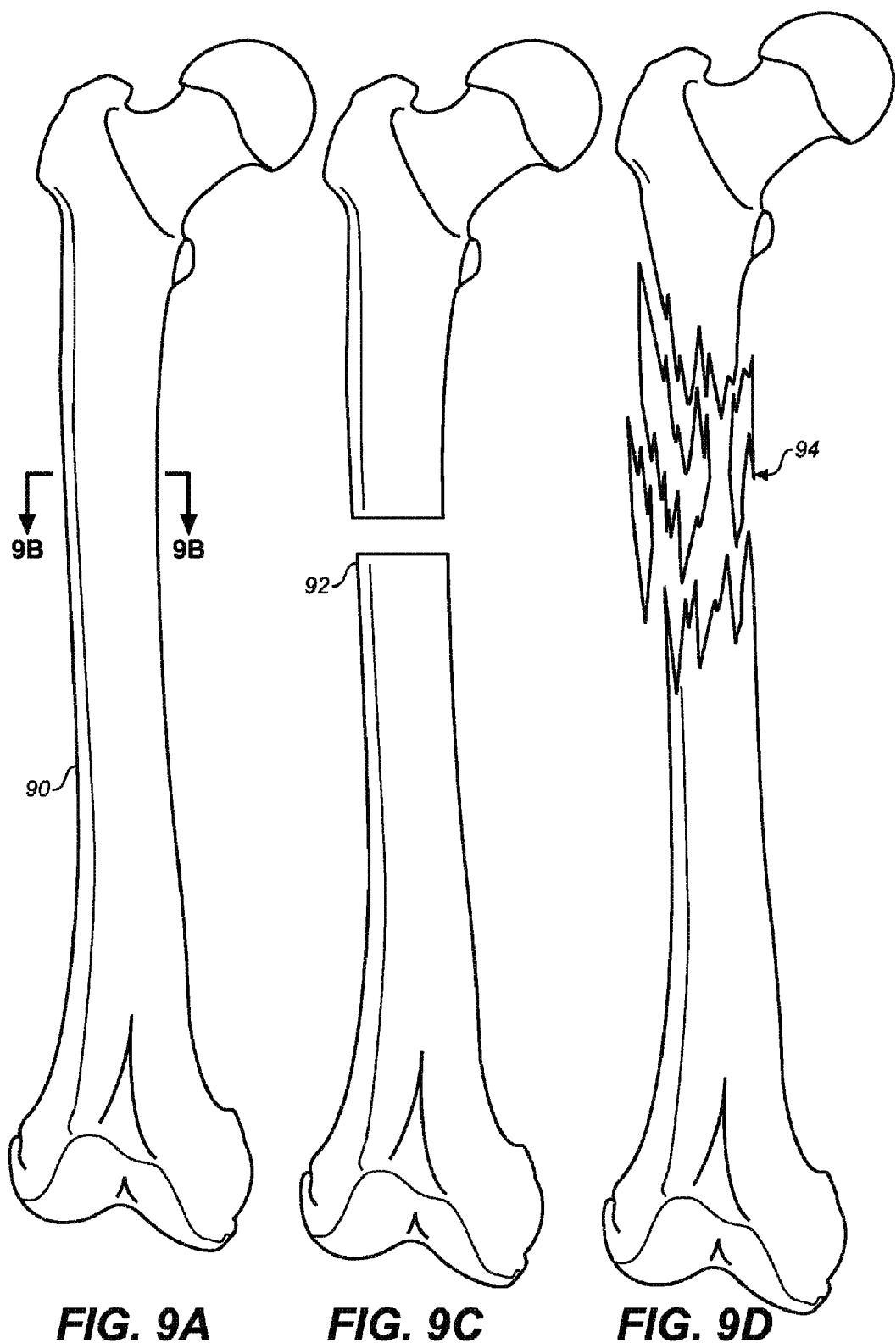
*FIG. 9A*  *FIG. 9C*  *FIG. 9D*

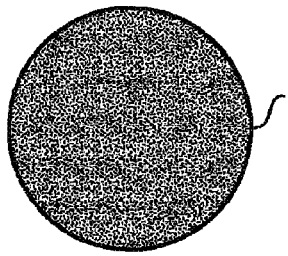
FIG. 9B
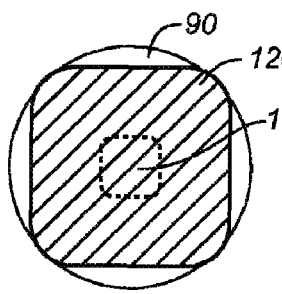
FIG. 10B
*(PRIOR ART)*
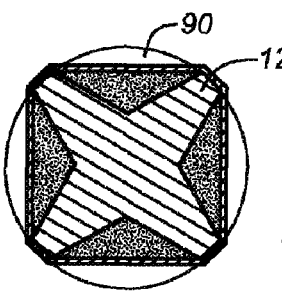
FIG. 11B
*(PRIOR ART)*
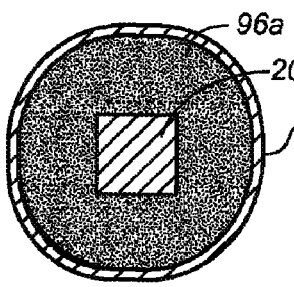
FIG. 12B
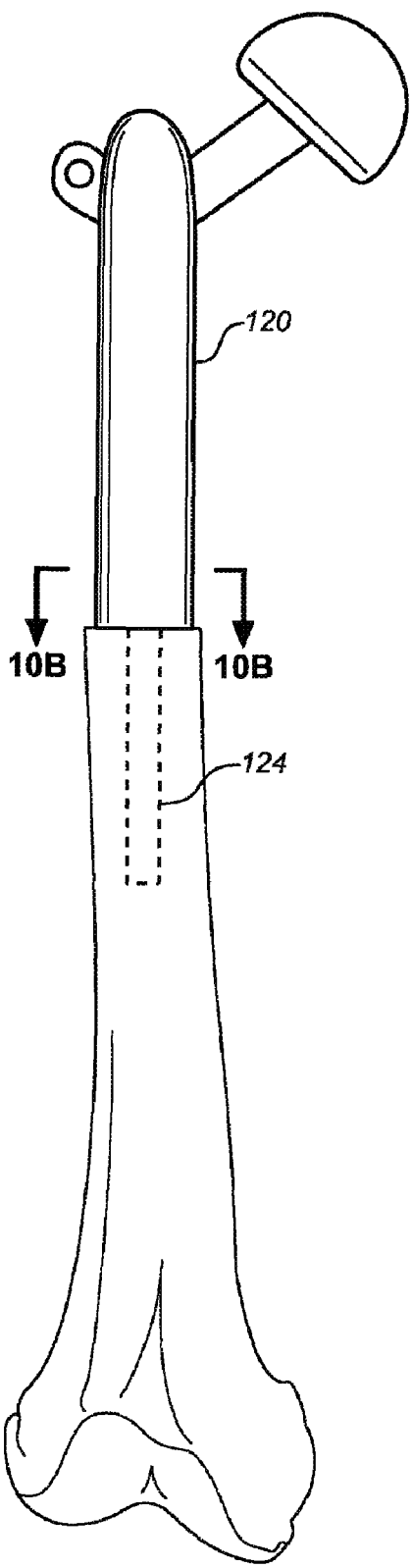
FIG. 10A *(PRIOR ART)*

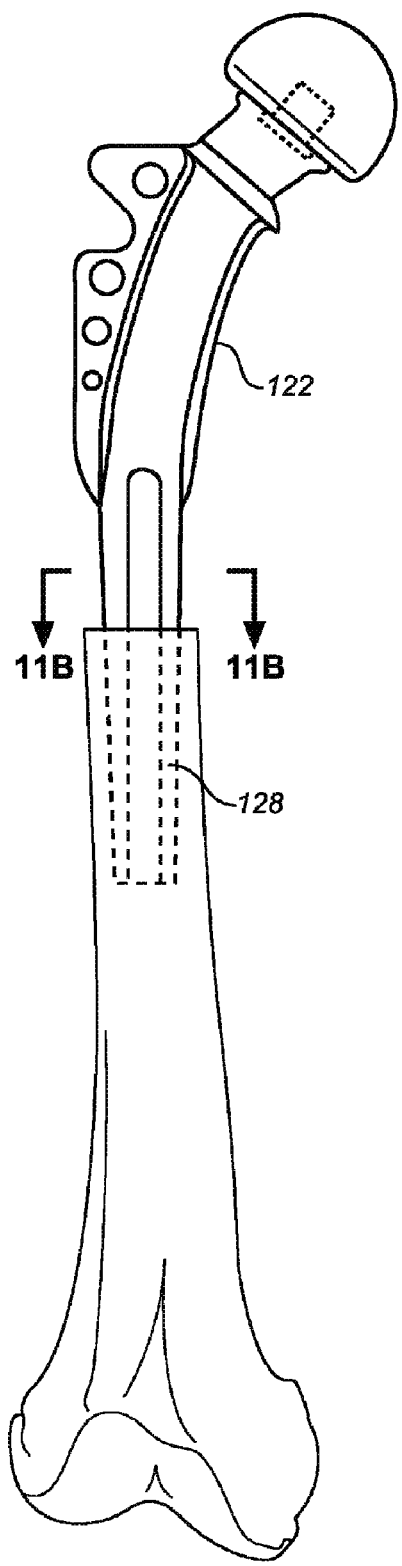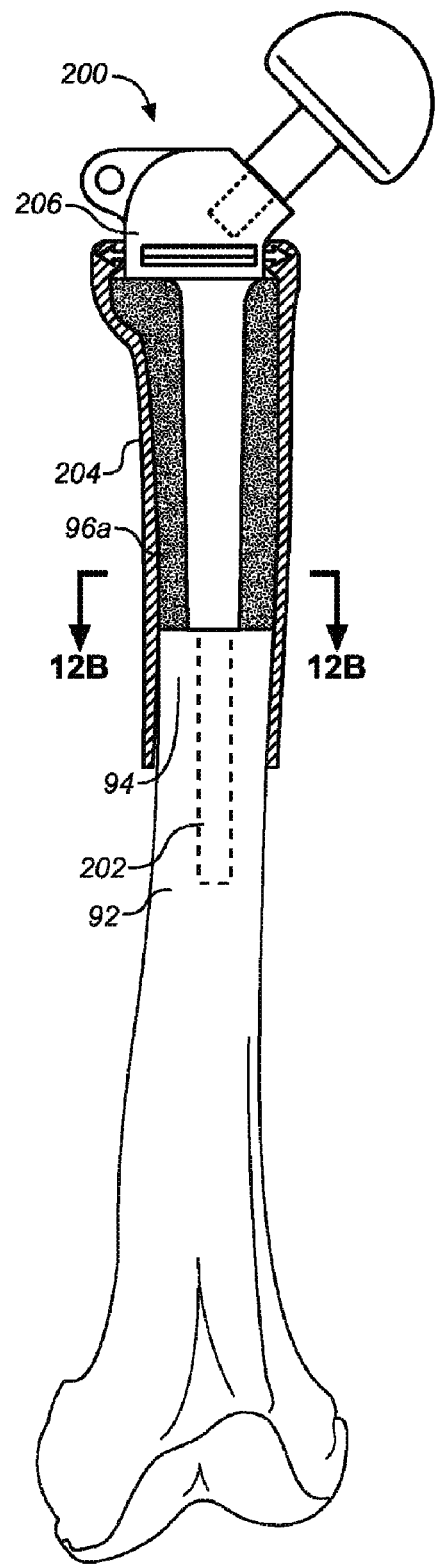
FIG. 11A *(PRIOR ART)*          FIG. 12A

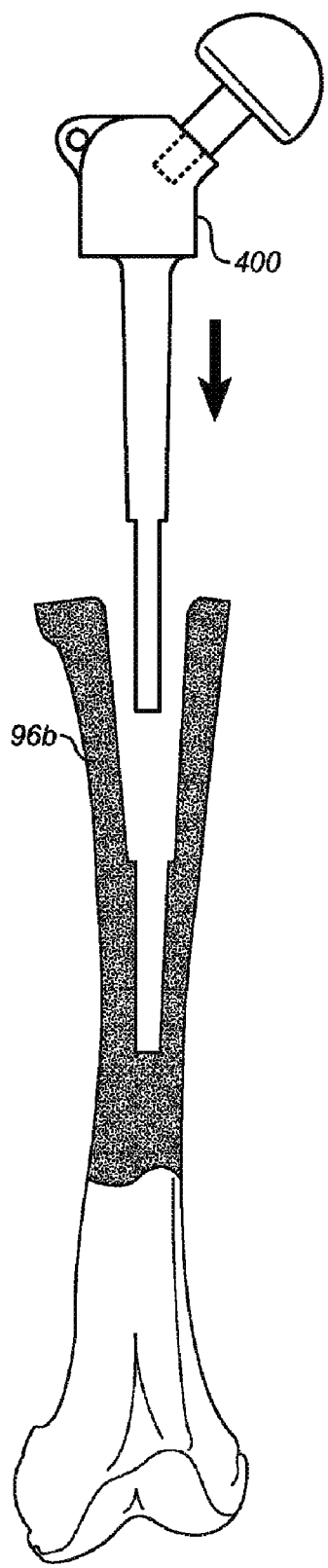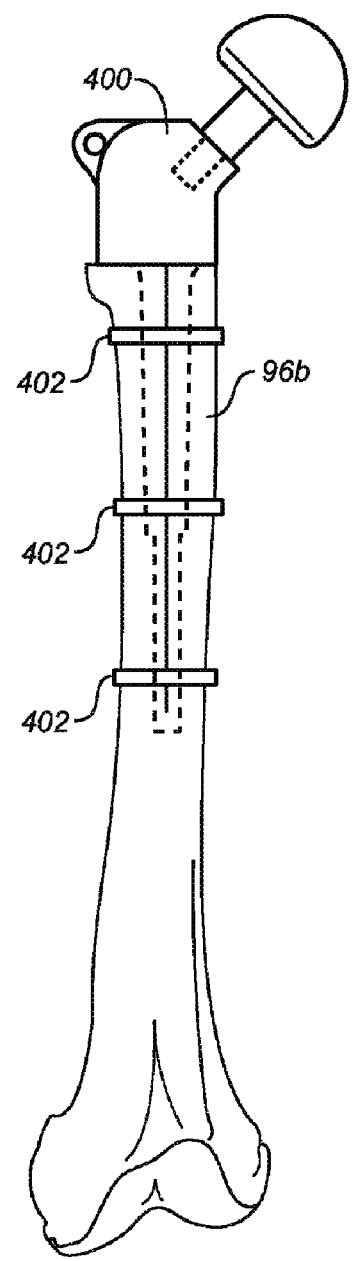
FIG. 16A  FIG. 16B

DEVICE AND METHOD FOR RECONSTRUCTION OF OSSEOUS SKELETAL DEFECTS

CROSS REFERENCES TO RELATED APPLICATIONS

The present application is a continuation-in-part application of U.S. Utility patent application Ser. No. 10/867,748, filed Jun. 16, 2004 (Jun. 16, 2004), which claims the benefit of the filing date of U.S. Provisional Patent Application Ser. No. 60/478,465, filed Jun. 16, 2003 (Jun. 16, 2003), each of which are incorporated in their entirety by reference herein.

SEQUENCE LISTING

Not applicable.

STATEMENT REGARDING FEDERALLY SPONSORED RESEARCH OR DEVELOPMENT

Not applicable.

THE NAMES OR PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

1. Field of the Invention

The present invention relates generally to implantable medical devices for the treatment of osseous skeletal defects, and methods for their use.

2. Background Discussion of Related Art

In the past, skeletal defects have required amputation due to the associated "flail extremity" which prohibited weight bearing due to skeletal insufficiency and lack of effective muscle power. Early in the twentieth century, Lexer popularized the transplantation of large human joint (allografts) for such problems. However, these have been associated with high rates of infections, non-unions, accelerated arthritis, and mechanical complications. With the advent of hip prosthetics as developed by Austin Moore's proximal femoral prosthesis in the 1940's and John Charnley's low friction arthroplasty (total hip arthroplasty) in the 1960's and early 1970's, some of these problems were addressed in the hip, eliminating the problem of allograft joint degeneration.

The total hip arthroplasty was later combined with allografts, forming an allograft prosthetic composite (APC), taking advantage of the healing potential between the allograft and the residual host bone as well as the relatively painfree articulation of the total joint replacement. Concurrently, segmental prostheses or "tumor prostheses" were developed. The APC and segmental prosthesis were particularly needed in the era of "limb-preservation surgery". This concept became possible with the development of chemotherapy agents that improved survival within the field of orthopedic oncology.

These allograft prosthetic composites (APC) were associated with high risks of infection and other complications. Massive osteoarticular allografts and APC's have a tremendous disadvantage due to some residual antigenicity and the slow incorporation of the allograft bone by host bone. The process termed "creeping substitution," whereby the allograft bone is replaced by host bone in an appositional fashion, leads to overall weakening of the graft. Large allografts have been shown to be an "admixture of necrotic and viable bone." This is in contrast to cancellous bone which based on its three dimensional porous architecture, facilitates bone ingrowth and increased mechanical strength after implantation.

Segmental prostheses are able to span the area of bone loss and are stabilized to the residual host bone. These prostheses, however, have several problems, including their large size, the high torques at the host-prosthesis interface, and risks of dislocation due to inadequate soft tissue attachments to the metal prosthesis. These issues are commonly found in the area of the knee and hip but also apply to the shoulder, elbow, ankle, and wrist. The search is ongoing for the ideal way to address a large segmental loss of bone adjacent to a large joint.

In some cases, due to bone loss resulting from infection or debris-mediated bone digestion, termed "osteolysis", the residual bone allows a contained defect with thin but relatively preserved walls. In such cases, a technique known as impaction grafting has been developed and used since the late 1970's. The osseous defect is serially filled with layers of cancellous bone graft, which interlock due to the force of impaction. Into this newly formed cavity, a cemented prosthesis can be inserted. As the cancellous bone graft incorporates, it restores the patient's bone stock and provides an ongoing stable bed for the cemented implant.

The common complications with the technique relate to the loss of fixation due to fracture of the host bone or lack of containment and interlock of the cancellous bed. In some cases where the host bone has a segmental defect, it can be bridged with an allograft strut or some other containment device. Alternatively, metal mesh has been used to contain the allograft. However, use of such mesh is ineffective in the event of complete deficiency of the native cortical shell due to the lack of containment of the bone graft at the end of the construct, i.e., at the hip joint in the case of a proximal femoral deficiency.

A first representative prior art method and apparatus are shown in FIGS. 10A-10B herein. Here there is shown a femoral component prosthesis for hip arthroplasty that includes an implant shaft with a generally square cross-sectional shape. The shaft of the prosthesis is inserted into the residual proximal end of a resected femur and secured, either with cement or a press fit. However, as will be readily appreciated from even a cursory inspection of the schematic drawing, once implanted this prosthesis provides no means whatsoever for the reconstitution of bone at the site of the prosthesis. More importantly, there is no means for forming a column of reconstituted bone that surrounds the prosthesis. Removal of this prosthesis leaves only the resected femur as prepared for the initial prosthesis.

An exemplary prior art method and apparatus are shown in French Patent Document 2,315,902, to Blanquaert, et al, which is shown in FIGS. 11A-11B herein, and which teaches a metal rod for insertion into a femur for a hip prosthesis. The rod has a cruciform cross-section with four rails or ribs that define hollow zones into which bone growth material may be placed to facilitate bone regeneration. However, the metal mesh that contains the bone growth material is welded to the ribs, and when the rod is placed in a femur, the tips of the ribs engage bone endosteum. Accordingly, the reconstructed bone does not produce a contiguous and complete column of bone that surrounds the prosthesis. On the contrary, any reconstituted bone must emerge in a configuration of generally parallel fingers or spikes spaced apart by gaps or slots in the column, and removal of the prosthesis entails the removal of all of the reconstituted bone. Accordingly, removal of the joint prosthesis will not result in a free standing column of bone suitable for use in further reconstructive surgery. This is a significant shortcoming in this prior art method.

BRIEF SUMMARY OF THE INVENTION

The present invention is a method and device that allows immediate stabilization of the extremity with a press-fit or cemented prosthesis fixed to the native bone. Surrounding the prosthesis is a potential space enclosed by a flexible member. The potential space is filled with bone graft materials such as cancellous bone chips, bone morphogenic proteins, etc. The factor distinguishing the present invention is that the circumferential cavitary space (i.e., hollow space) around the implant which allows the reformation of an entire bony network. This is because the cavitary space is a single, unitary potential space, which when filled with a volume of osteoconductive material creates a monolithic or single volume that closely matches normal bony architecture, with continuous and contiguous material around a portion of both the implantable portion of the apparatus and the proximal prosthetic portion of the apparatus. Stated another way, the cavitary (hollow) space is not interrupted by any prosthetic structure that divides the volume of the cavitary space into discrete and separate volumes. This features is different from and superior to that seen with allograft prosthetic composites which contain a structural, cortical allograft. It distinguishes over prior art devices that form a plurality of cavitary spaces around an implant element but which do not provide means to reconstitute normal bony architecture. In the present invention, as the bed of particulate bone graft matures, it is gradually exposed to increasing stresses to encourage remodeling and maturation into normal bony architecture.

The material comprising the flexible member can be selected from a variety of suitable materials, including those that are metabolized and resorbed over time. As the bone matures, vascular channels ingrow through the flexible membrane into the reconstituted bone as the flexible member resorbs. Thus, over time a fully reconstituted bone with a cortical and cancellous segment will form. Should the implant fracture or fail due to other reasons such as polyethylene wear, infection, or loosening, the implant can be removed with a variety of techniques common in the art of orthopaedic surgery. The reconstituted bone will remain and will allow future treatment options, such as reimplantation of a joint arthroplasty either at the same time or in a staged fashion.

Additional advantages and features of the present invention will be apparent from the following drawings, detailed description and examples which illustrate preferred embodiments of the invention.

BRIEF DESCRIPTION OF THE DRAWINGS

FIG. 2 is an upper front perspective views of an embodiment of the inventive femoral component for a total hip arthroplasty;

FIG. 3 is an upper rear perspective views of the femoral component of FIG. 2, shown with a flexible member installed to create a cavitary space to be configured around osteoconductive material;

FIGS. 4A-4D are schematic drawings showing an acetabular reconstruction using an implantable device of the present invention, wherein FIG. 4A illustrates an acetabular implant, FIG. 4B illustrates a bone defect in a patient's hip socket, and FIGS. 4C-4*d* depict the acetabular implant positioned in a patient's hip socket;

FIG. 9A is a schematic side view in elevation showing a bone—in this case a human right femur;

FIG. 9B is a cross-sectional view of the bone of FIG. 9A taken along section line 9B-9B;

FIG. 9C is a schematic view showing a resection of the proximal femur (top) from the residual femur of the bone of FIG. 9A;

FIG. 9D is a schematic side view in elevation showing the femur of FIG. 9A with a comminuted fracture;

FIG. 10A (Prior Art) is a schematic view showing a resected femur with a common prior art prosthesis installed;

FIG. 10B (Prior Art) is a schematic cross-section of FIG. 10A taken at 10B-10B;

FIG. 11A (Prior Art) is a side view in elevation showing a resected femur with another common prosthesis installed and after bone growth has occurred;

FIG. 11B (Prior Art) is a cross-sectional view of FIG. 11A taken at 11B-11B;

FIG. 12A is a schematic cross-sectional view showing a resected femur with a prosthesis of the present invention installed and after bone growth has occurred;

FIG. 12B is a cross-sectional view of FIG. 12A taken at 12B-12B;

FIG. 13A is replaced with a new (second) prosthesis;

FIG. 16A is a schematic cross-sectional side view in elevation of the femur showing the installation of a replacement prosthesis for the prosthesis removed in FIG. 15B;

FIG. 16B shows the replacement prosthesis installed with radial banding of the bone of the femur shown in FIGS. 15A-16A;

DETAILED DESCRIPTION OF THE INVENTION

Reference will now be made in detail to the presently preferred embodiments of the invention, which, together with the following examples, serve to explain the principles of the invention. These embodiments are described in sufficient detail to enable those skilled in the art to practice the invention, and it is to be understood that other embodiments may be utilized, and that structural, chemical, and biological changes may be made without departing from the spirit and scope of the present invention.

The present invention is an implantable device comprising a prosthesis and a flexible member attached to the prosthesis by means of one or more attachment members, where the flexible member is arranged around the prosthesis to form a cavitary space. The cavitary space is then filled with a variety of osteoconductive and osteoinductive materials. The present invention facilitates the restoration of bone loss, including bone loss adjacent to a joint, by providing structural support, bone ingrowth, and durability.

The prosthesis may be any skeletal prosthesis, such as a joint arthroplasty implant, modified by the addition of attachment members to facilitate attachment of the flexible member thereto. The present invention can be utilized with any type of orthopaedic implant as long as the desired position of the implant facilitates attachment of the attachment member. Orthopaedic prostheses are manufactured by a large number of medical device manufacturers. Most mechanical prostheses in current use in total joint replacements are manufactured from alloys such as cobalt-chromium, or are made of titanium.

If a standard orthopaedic prosthesis is used in the methods of the present invention, it is modified to attach an attachment member to the prosthesis. One embodiment of an attachment member includes the use of metal rails welded to the prosthesis to which a flexible member can be interlocked at one end and then banded to the residual host bone at the other end. Other methods of attachment can be with the use of screws, pins, bands, and/or sutures to interlock the flexible member to the prosthesis.

The prosthesis can be fixed into the patient's native skeleton. In the case of a joint prosthesis, the articulating surface is stabilized at a given distance from the residual bone to reconstruct the joint at the appropriate level. The prosthesis can be embedded in the host bone using any mechanical fixation necessary. Modes of fixation can be with the use of methylmethacrylate bone cement or by ingrowth of bone into the prosthesis.

Figure 1A:
FIGS. 1A, 1B, and 1C illustrate cross-sectional, top, and perspective views of an embodiment of a flexible member of the present invention.
Figure 1B:
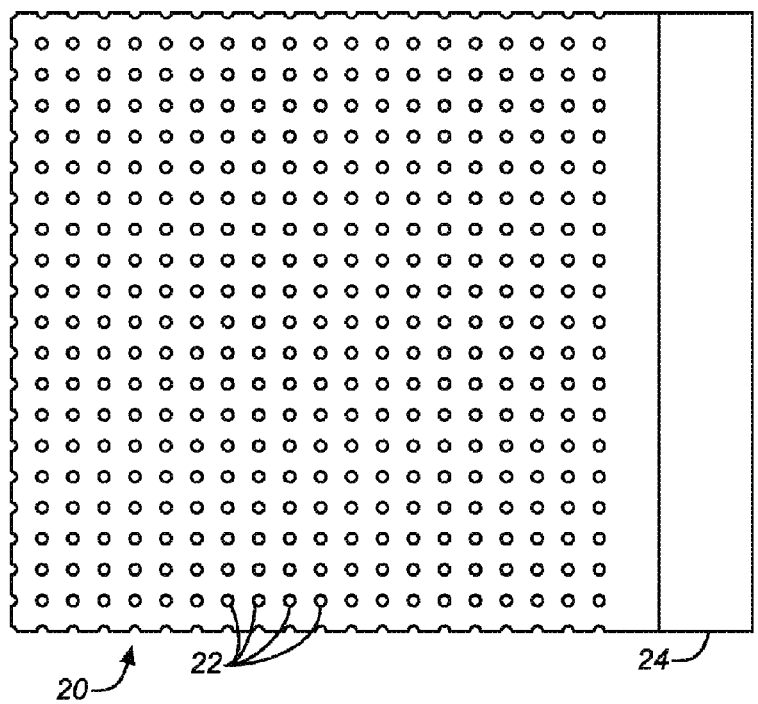
Figure 1C:
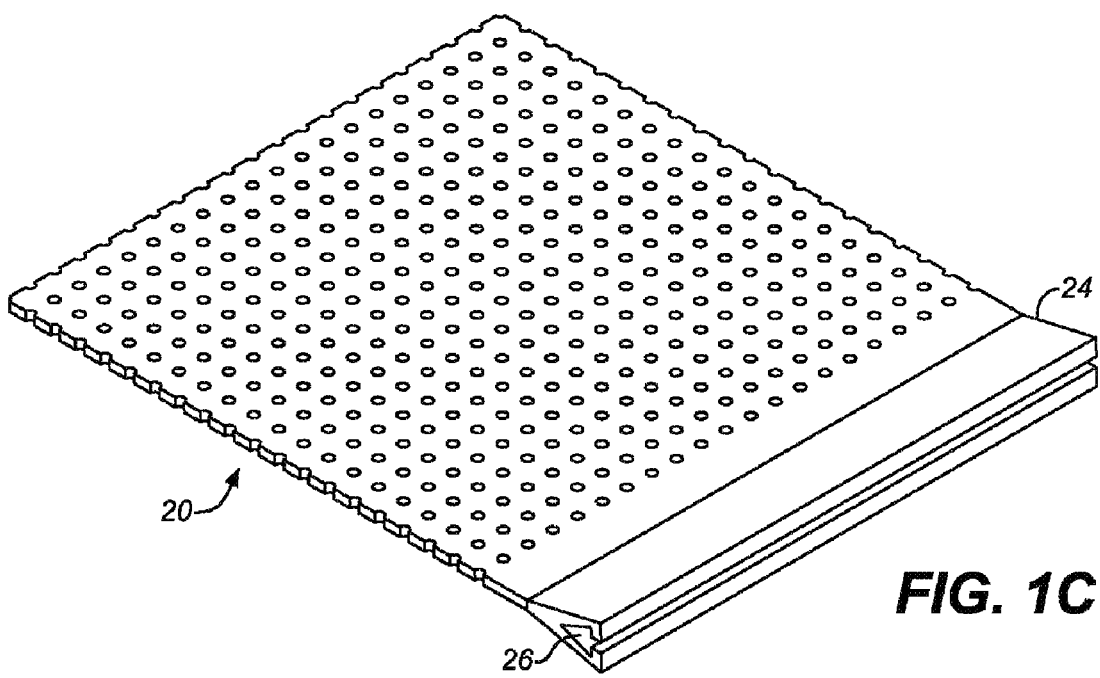
Figure 6:
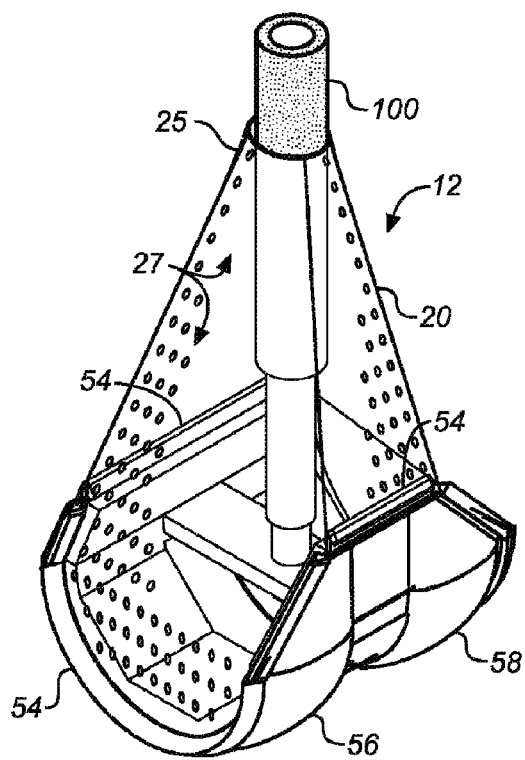
FIG. 6 is an upper perspective view of the femoral component of FIGS. 5A-5C, shown with a flexible member attached for creating a cavitary space for osteoconductive material.
Figure 5B:
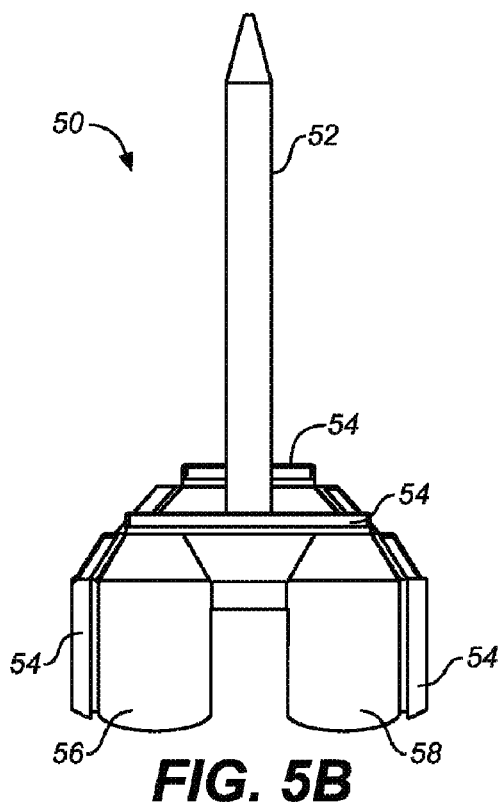
Figure 5C:
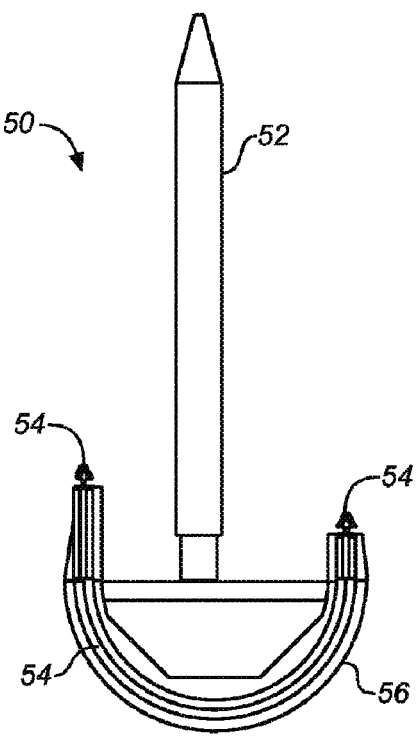
Figure 8:
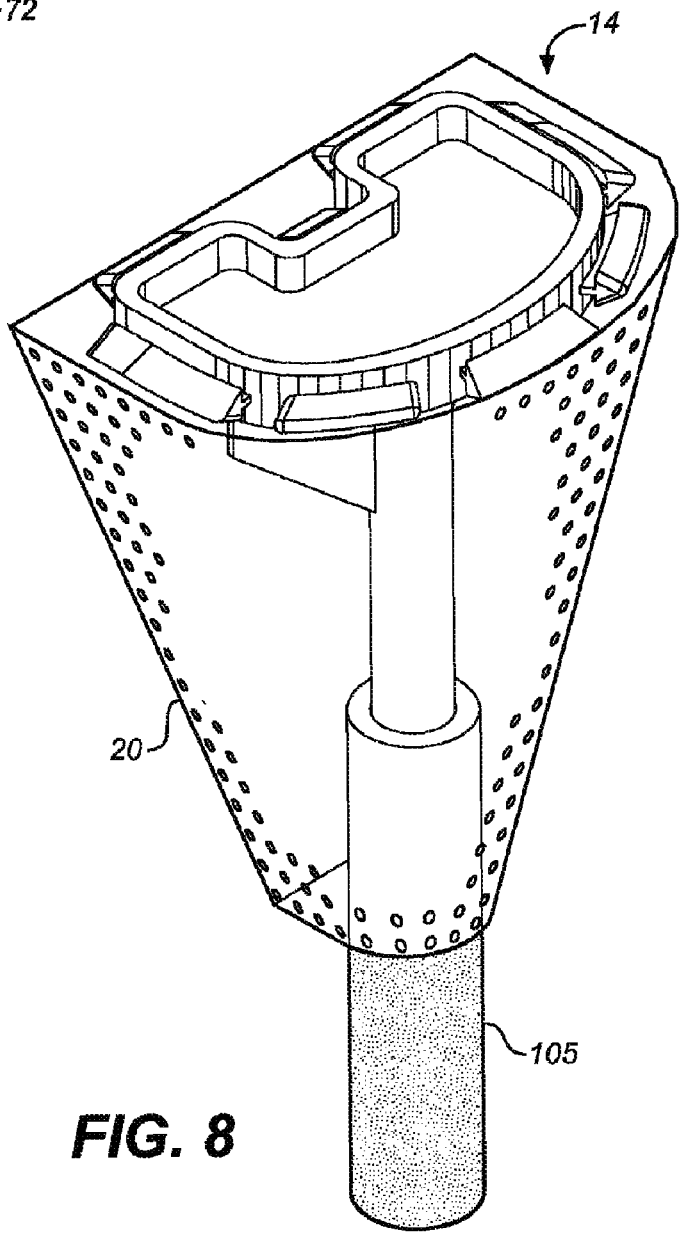
FIG. 8 is an upper front left perspective view of the tibial component of FIG. 7, shown with a flexible member attached.

Referring now to the Figures, and especially FIGS. 1A-1C, the flexible member 20 may have any suitable generic shape, such as that of a oblong sheet or mesh (as can be seen in FIGS. 1B and 1C), or it may be particularly shaped to fit a particular prosthesis (as shown in FIGS. 3, 6, and 8). Regardless of its shape, the flexible member 20 is perforated to allow ingress of blood vessels during the maturation process of the reconstituted bone. The perforations (or holes) 22 are preferably sized between approximately 100 to about 2000 microns in diameter and are spaced at a distance of approximately 1000 to 10,000 microns depending on the specific application. Although the perforations 22 shown in FIGS. 1B and 1C are regularly spaced and of substantially the same size, they may be randomly placed, and may be of varying sizes. In other embodiments, the flexible member 20 may be a fibrous network or a wire mesh, instead of as a perforated sheet.

The flexible member is sufficiently pliable and flexible to permit a surgeon to contour and configure the flexible member and to make appropriate adjustments during implantation to address the exact needs of the procedure, but it need not be flexible after implantation, and may, for example, be treated after shaping and/or implantation to retain a particular shape (such as, for example, by UV curing). After implantation, the flexible member must have sufficient tensile strength to maintain its attachments to the prosthesis and to the host bone, particularly when filled with the osteoconductive and osteoinductive bone graft material.

As desired for a particular application, the flexible member may be bioresorbable or non-resorbable, and may be fabricated from several suitable materials, including metal, a biomaterial such as demineralized bone matrix, or a polymer. In a preferred embodiment, the flexible member is formed of a resorbable polymer such as polylactic acid (PLA), polyglycolic acid (PGA), collagen, hyaluronate, demineralized bone matrix, or any one of a number of other flexible or semi-rigid materials.

For many applications, a resorbable flexible member is preferred. During the maturation process of the contained bone graft material, a resorbable flexible member will be nearly completely metabolized, while still providing a framework for reconstituting an outer periosteal layer for the new bone and to allow further vascular perforation of the bone graft. In other applications, a non-resorbable flexible member such as metal mesh is preferred. These circumstances include cases in which mechanical loading of the flexible member is required. For example, in the case of an acetabular reconstruction, a flexible member composed of wire mesh rather than a resorbable polymer can be used to contain the bone graft under high compressive pressure until it matures around a porous ingrowth acetabular (hip socket) component.

The flexible member is attached to the prosthesis by means of one or more attachment members, non-limiting examples of which include rails, runners, and suture holes. In a preferred embodiment, the prosthesis has triangular rails affixed in key locations, and the flexible member has a prosthetic margin designed to match or mate with the triangular rails. The shape of the rails, and the corresponding shape of the prosthetic margin, is not limited to a triangular cross-section, but may be any suitable geometric shape allowing for a secure interlock.

Referring once again to FIG. 1, the prosthetic margin 24 can be formed by a thickening of the flexible member 20 with a receptacle 26 for the triangular rails of the prosthesis. The receptacle 26 has a cross-sectional geometry substantially identical to the attachment member (e.g., rails—see element 32 in FIGS. 2-3), though with slightly larger dimensions so as to allow interlocking of the sheet to the rails. Alternatively, the flexible member 20 can be fixed to the prosthesis (not shown in this FIGS. 1A-1C) with some other form of fixation such as an adhesive, suture or clip.

In a preferred method of use, the prosthesis is first fixed to the patient's host bone by standard surgical means. After initial stabilization of the prosthesis to the host is achieved, the flexible member is wrapped around the prosthesis by attaching it to one or more attachment members on the prosthesis and configured to define a cavitary space, the volume of which comprises the space generally enclosed by the flexible member and located between the outer surface of the prosthesis and the inner surface of the flexible member. The cavitary space is partly contoured to the satisfaction of the surgeon and left open on the host bone engaging end. It is then filled with any of a variety of osteoconductive and osteoinductive materials. Non-limiting examples of such materials include autologous bone graft (from the patient), cancellous bone allograft (from a cadaver donor), and bone graft substitutes such as calcium sulfate, calcium carbonate, calcium phosphate, hydroxyapatite, demineralized bone, and/or bone morphogenic protein (BMP). Calcium sulfate is available from Wright Medical (Arlington, Tenn.), hydroxyapatite is available from Interpore-Cross (Irvine, Calif.), and demineralized bone and bone morphogenic protein are available from Stryker (Kalamazoo, Mich.). Calcium carbonate and calcium phosphate are available from standard medical suppliers.

After the cavitary space is filled, the flexible member is attached to the host bone using resorbable or non-resorbable clips, pins, screws, cables, or bands, thereby containing the bone graft and allowing it to mature around the prosthesis. In a preferred method, a resorbable bone screw with a thread matching the specific sheet pore size (for pore sizes greater than 1000 microns), is used to attach the flexible member to the host bone.

The outer surface of the metal prosthesis is composed of an ingrowth surface which can be fabricated from porous metal, ceramic, or other surface materials. This allows stable fixation to the host residual bone. The contained bone graft matures in a pattern dictated by the contour of the flexible member, healing to the residual host bone and optimally achieving ingrowth or ongrowth onto the prosthesis. Thus, it reconstructs the osseous defect from the level of the residual host bone to the level of the upper end of the prosthesis adjacent to the joint at the opposite end of the device and thereby results in a circumferential reconstitution of bone.

In essence the flexible member acts as a periosteum, dictating the shape and size of the reformed bone adjacent to the articulating surface, tooth, or artificial disc implant. As this bone graft is loaded around the prosthesis, it is exposed to stresses that further drive it to remodel according to Wolff's Law, which describes the tendency of bone to respond with increased density and strength when exposed to a compressive load. The flexible member affords additional stability around the bone graft by containing it and providing a column of support from the residual bone to the articulating portion of the prosthesis, thus highlighting a unique feature of the method of the present invention, which is that it effects a circumferential reconstitution of bone.

Application of the teachings of the present invention to a specific problem or environment is within the capabilities of one having ordinary skill in the art in light of the teachings contained herein. Exemplary embodiments of the products and processes of the present invention appear in the following examples.

EXAMPLE 1

Femoral Resection

Referring next to FIGS. 2 and 3, the present invention is utilized in resection of a proximal femoral osteosarcoma in a 15 year old male. FIG. 2 illustrates a femoral prosthesis 30 of the present invention, and FIG. 3 illustrates an implantable device 10 comprising the femoral prosthesis 30 surrounded by a flexible member 20. The implantable device 10 is used to reconstruct the proximal femur of a patient (not shown) in a five-step process. This process is adaptable for use, as will be evident to those of skill in the art, within any of the large joints including the hip, knee, shoulder, elbow, and ankle.

First, a prosthesis 30 is selected for use, with consideration given to the appropriate height and diameter of the stem 34 in order to achieve adequate fixation, leg length restoration, and soft tissue tension in the extremity. The prosthesis 30 is provided with one or more attachment members 32. In this instance, rails are placed circumferentially around the proximal end of the prosthesis. The stem 34 of the prosthesis 30 is implanted into the host bone 100 using customary surgical practices, such as the use of press-fit or with bone cement.

Second, a flexible member 20 is provided for use with the prosthesis 30, and this flexible member is constructed and shaped to match the planned three-dimensional shape and structure of the reconstructed proximal femur, i.e., a greater and lesser trochanters. The flexible member 20 is affixed to the attachment members 32, such as by mechanically bonding, i.e., interlocking, the prosthetic margin 26 (as shown in FIG. 1) onto the attachment members 32. Then, the flexible member 20 is wrapped or tubularized around the prosthesis 30 to form a cavitary space 21 between the flexible member 20 and the prosthesis 30. Any excess flexible member 20 may be trimmed or cut.

Third, tendons (not shown), such as the hip abductors in the femur or patellar tendon in the tibia, are attached to the implantable device 10. Either the tendon as a soft tissue structure, or with its bony attachment, is attached with standard techniques, as with sutures or wires, to the flexible member 20 or to the prosthesis 30. If the tendon is attached to the prosthesis 30, it is first passed through an aperture 28 in the flexible member 20. The attachment of the tendons facilitates the formation of Sharpey's fibers into the reconstituted proximal femoral bone.

Fourth, the cavitary space 21 formed between the flexible member 20 and the prosthesis 30 is filled with osteoconductive or osteoinductive material. Non-limiting examples of suitable filler material include autologous bone graft, cancellous bone allograft, and bone graft substitutes such as calcium sulfate, calcium carbonate, calcium phosphate, demineralized bone, and/or bone morphogenic proteins.

Fifth, and finally, the free margin 23 of the flexible member 20 is attached to the host femur 100. Fixation is achieved by suitable surgical means known to those of skill in the art, including drill holes and sutures, a circumferential band, small resorbable screws, or any method that will maintain the containment of the bone graft within the flexible member and define the volume for the resulting circumferential reconstitution of bone.

EXAMPLE 2

Acetabular Reconstruction

Figure 4A:
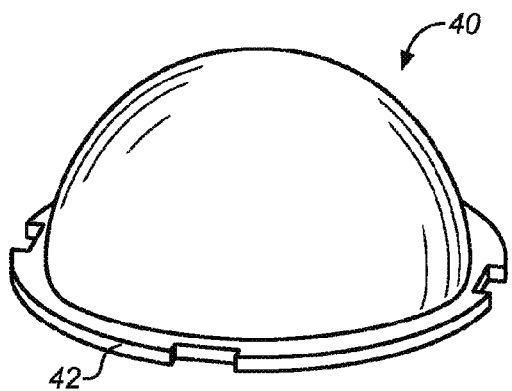
Figure 4B:
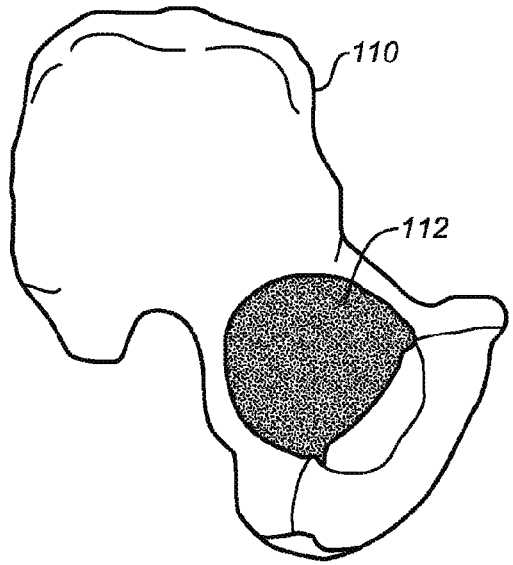
Figure 4C:
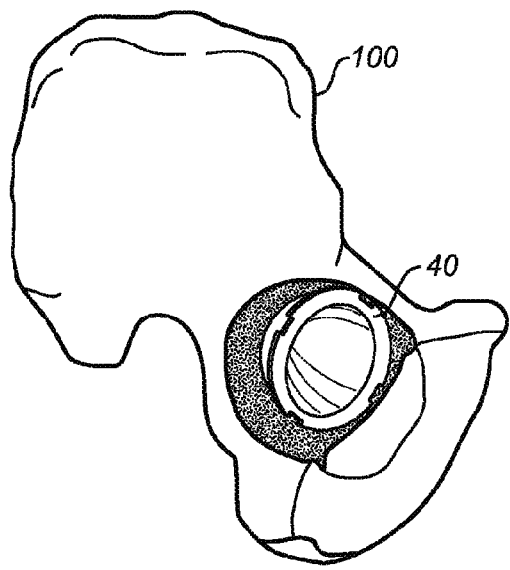

With reference next to FIGS. 4A-4D, the present invention may be used to treat a large superior defect of the acetabulum 112 in the case of hip dysplasia or in the revision setting. FIG. 4A shows the porous surface of an uncemented acetabular cup prosthesis 40 with peripheral attachment members 42 disposed proximate the rim of the hemispherical prosthesis. FIG. 4B depicts a patient's iliac wing 110 and acetabulum 112, the latter having a large superior dome defect. As shown in FIG. 4C, the cup 40 is placed in the acetabulum and can be fixed to the residual acetabulum using a combination of press-fit with available bone, or with acetabular screws, or using a combination of modular cup attachments and screws placed into the ilium, ischium, and pubis.

Figure 4D:
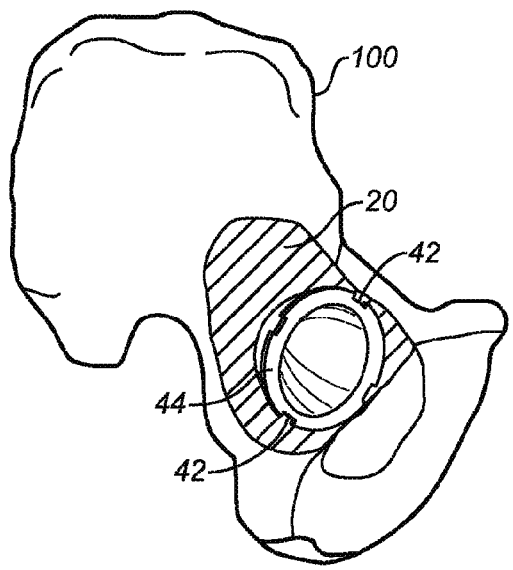

The residual bone loss is reconstituted by attachment of the flexible member 20 to the margins 42 of the cup 40 with attachment members 44, as shown in FIG. 4D, and by filling the resultant cavitary space with osteoconductive and osteoinductive bone graft material, as described in Example 1. This bone graft has the potential to mature into a vascularized bed that can grow into the porous surface of the prosthesis and also facilitate any future acetabular revision surgeries. The free margins of the flexible member 20 are then attached to the ilium using bioabsorbable or metal screws.

EXAMPLE 3

Total Knee Arthroplasty

Figure 5A:
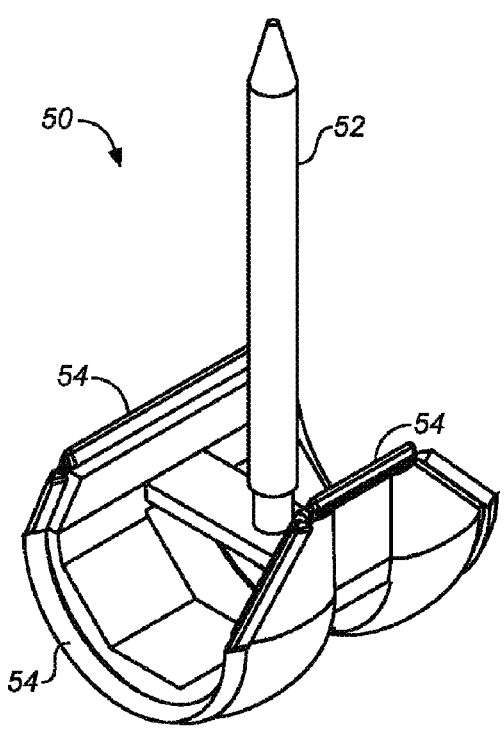
FIGS. 5A-5C are upper perspective, rear elevational, and side elevational views of the inventive femoral component for total knee arthroplasty of the present invention.

With reference next to FIGS. 5A through 8, a total knee arthroplasty with a comminuted supracondylar fracture with major bone loss is treated with a long press-fit intramedullary revision femoral component embedded in the residual femoral diaphysis. FIGS. 5A through 5C illustrate a femoral prosthesis 50 of the present invention, and FIG. 6 illustrates an implantable device 12 comprising the femoral prosthesis 50 surrounded by a flexible member 20. The implantable device 12 is used to reconstruct the distal femur of a patient (not shown) in a multi-step process.

The process described in Example 1 is adapted for use on the distal femur, wherein first a prosthesis 50 is selected for use, with consideration given to the appropriate height and circumference of the stem 52. The prosthesis 50 is provided with rounded artificial articular surfaces 56, 58, simulating the medial epicondyle and medial condyle of the femur and the lateral epicondyle and lateral condyle of the femur, to which one or more attachment members 54, to which the flexible member 20 is attached. The proximal margins 25 of the flexible member 20 are fixed to the outer surface of the femoral diaphysis 100, thereby defining a partially enclosed cavitary space 27 which is then filled with cancellous bone allograft and bone morphogenic protein. The cancellous bone matures over time and achieves bone fixation to the prosthesis ingrowth surface, thereby avoiding the use of an allograft and restoring native bone.

Once native bone is restored in a columnar configuration, the prosthesis may be removed while leaving the bone column for further prosthetic implants. This is a significant departure from prior art prosthetic devices, which produce a bone graft contained at least partly on, in, and within the prosthetic structure, such that removal of the prosthesis will result in complete structural failure of the reconstituted bone.

Figure 7:
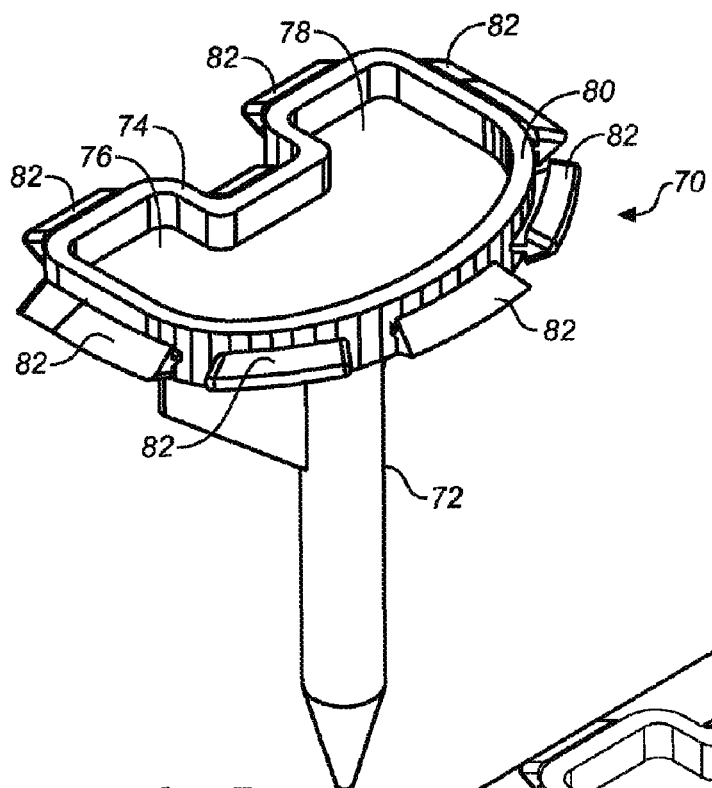
FIG. 7 is an upper front left perspective view of the tibial component for total knee arthroplasty of the present invention.

FIGS. 7 and 8 illustrate the tibial component of the total knee arthroplasty. FIG. 7 shows the tibial prosthesis 70, and FIG. 8 illustrates an implantable device 14 comprising the tibial prosthesis 70 surrounded by a flexible member 20. The tibial component includes a shaft portion 72 for insertion into the proximal end of a resected tibia 105, and a proximal head 74, which includes a first recess portion 76 that serves as the articular surface of the lateral condyle of the tibia and a second recess portion 78 that serves as the articular surface of the medial condyle of the tibia. The proximal head 74 includes a rim 80 circumscribed by a plurality of attachment members 82 (e.g., rails) suitable for use in the fixation of a flexible member.

The implantable device 14 is used to reconstruct the tibia of a patient (not shown) in a multi-step process as described above and in Example 1.

FIGS. 9A through 18B illustrate the essential ways in which the present invention advances over the prior art. FIG. 9A shows a human right femur 90, while FIG. 9B is a cross-sectional view of the same bone taken at line 9B-9B of FIG. 9A. FIG. 9C is a schematic view showing the bone of FIG. 9A resected 92, and FIG. 9D shows the femur of FIG. 9A with a comminuted fracture 94 of the kind that could call for a total hip arthroplasty.

FIGS. 10A-11B show two kinds of prosthetic femoral components 120, 122 employed in prior art hip arthroplasty. FIGS. 10A-10B show a prosthesis having an implant shaft 124 with a generally square cross-sectional shape. FIGS. 11A-11B show a prosthesis having an implant shaft 128 with a cruciform or cross-shaped cross-sectional shape. As discussed in the Background Discussion of Related Art, above, once implanted neither prosthesis provides a means for forming a column of reconstituted bone that entirely surrounds even the implanted prosthetic shaft. Further, neither prosthesis can be removed in such a way that the removal leaves a complete column of reconstituted bone suitable for use in subsequent reconstructive surgery.

In contrast, the present invention is a new and improved surgical method and prosthetic apparatus 200 for complete synovial joint osteotomy that provides means, firstly, for the immediate stabilization of an extremity with a press-fit or cemented prosthesis that uses a prosthesis having an implantable rod 202 and a cooperating porous flexible member 204 that creates a potential space around the implantable rod and up to the level of the articular head 206 of the prosthesis for the placement of bone graft materials 96a (see esp. FIG. 12A). This circumferential potential space entirely surrounds the implant rod and at least a portion of the articular head and facilitates the reformation of an entire bony network that is exposed to load-bearing forces that foster remodeling and maturation into normal bony architecture. The flexible member is preferably fabricated from material that is metabolized and resorbed, and as the bone matures and is vascularized with ingrowth through the flexible member, over time a fully reconstituted bone with a cortical and cancellous segment is formed. If the implant must be removed for any reason, it can be removed and a new implant installed in the column of reconstituted bone. This provides surgeons with important treatment options, including a reimplantation of a subsequent complete joint arthroplasty.

Figure 13A:
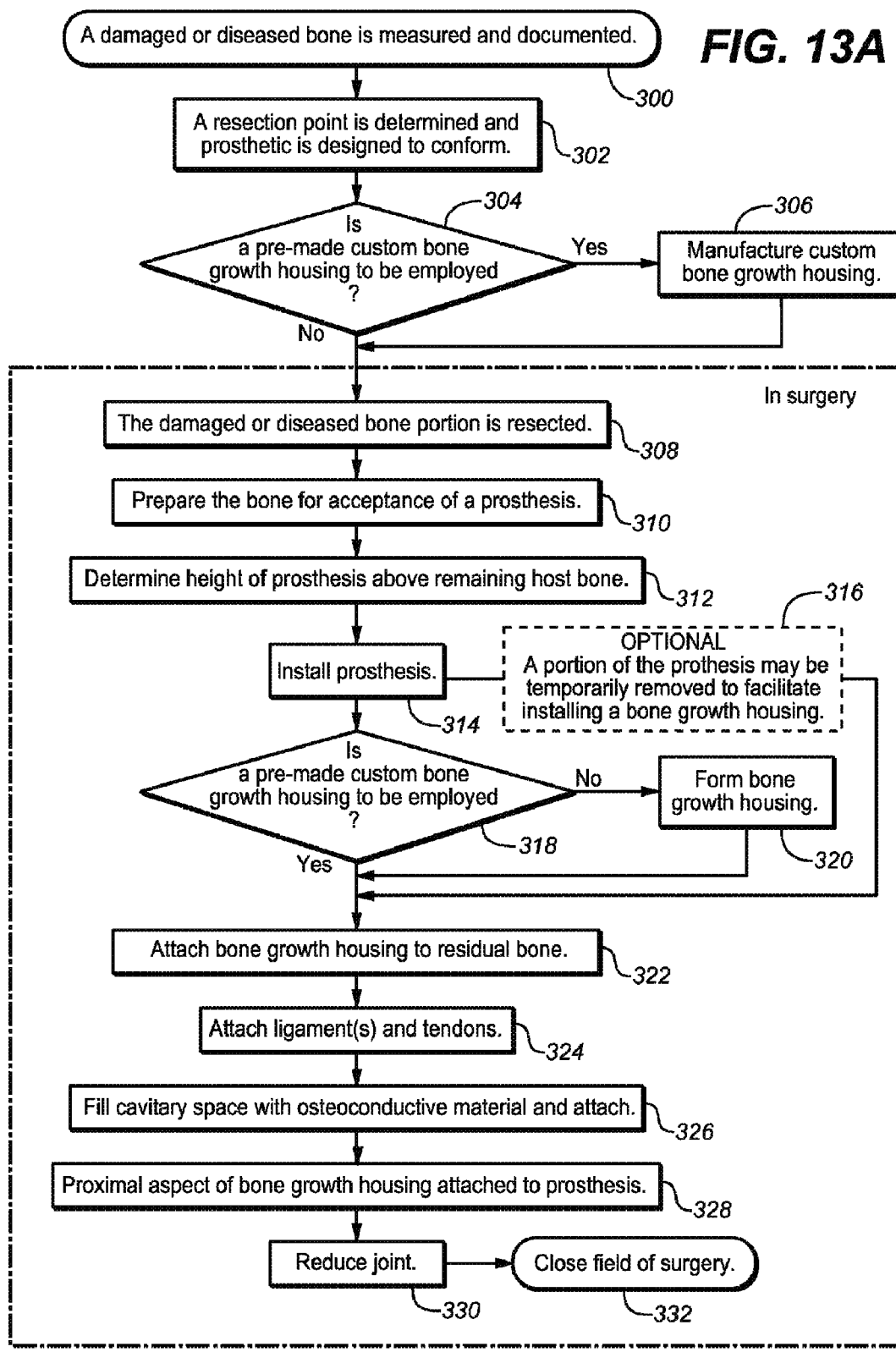
FIG. 13A is a flow chart of the method steps of the present invention when the prosthesis of FIG. 12A is initially installed.
Figure 13B:
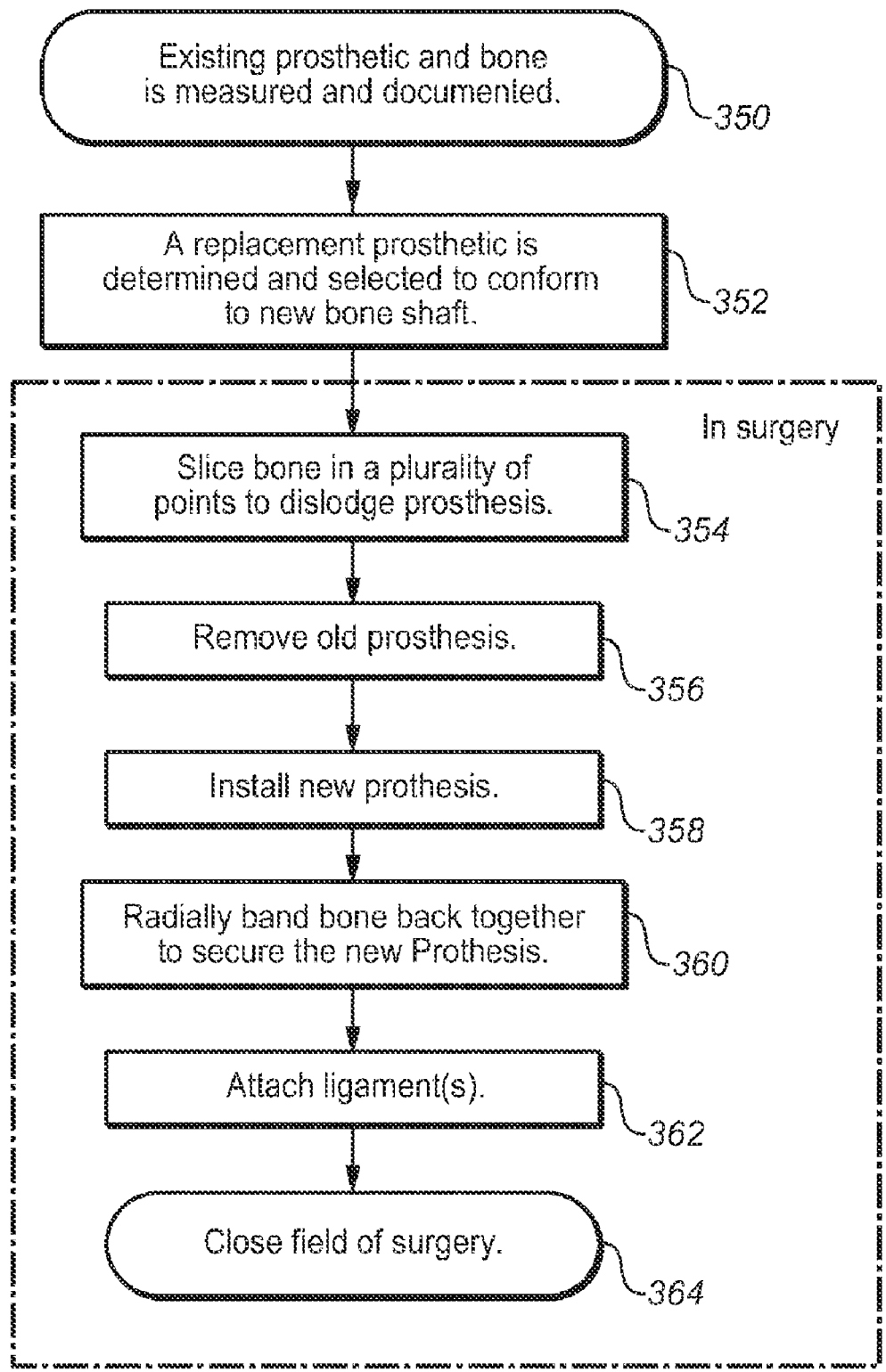
FIG. 13B is a flow chart of the method steps of the present invention when the initial prosthesis
Figure 14A:
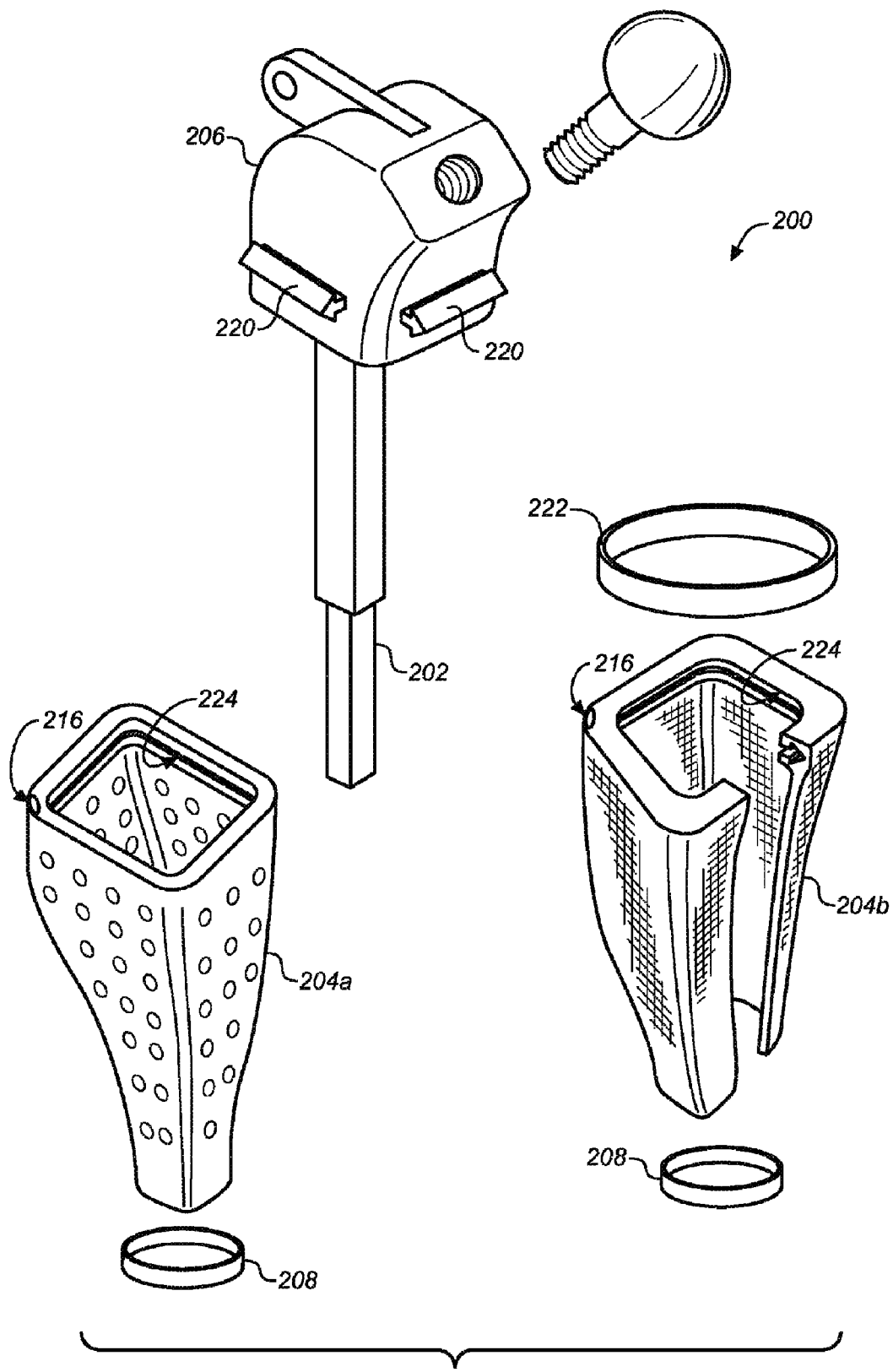
FIG. 14A is an exploded perspective view of the inventive apparatus employed when carrying out the method steps shown in FIG. 13A.
Figure 14B:
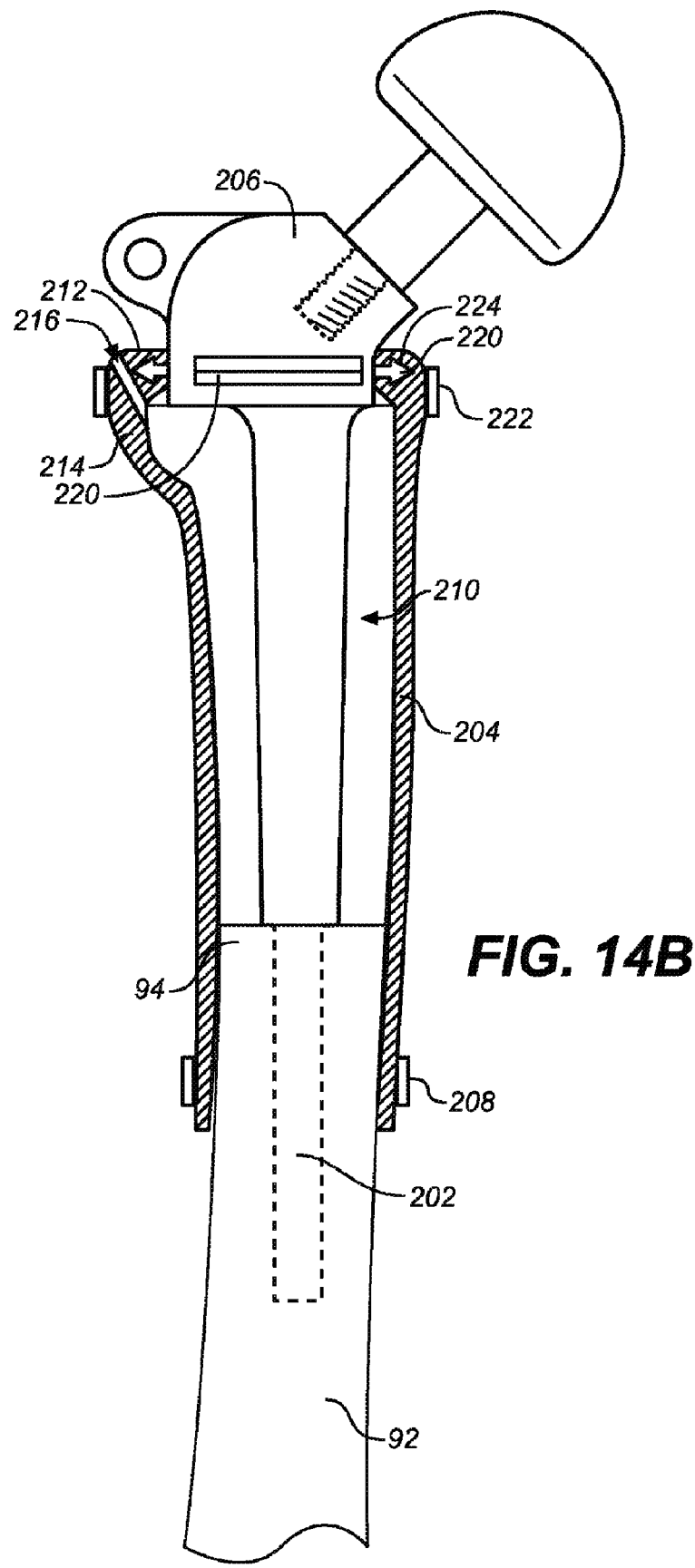
FIG. 14B is a schematic cross-sectional view in elevation of the prosthetic apparatus and flexible member of FIG. 14A installed in a properly prepared femur.
Figure 15C:
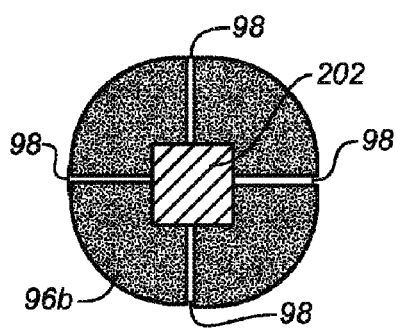
FIG. 15C is a cross-sectional view of the femur and prosthesis of FIG. 15A taken at 15C-15C, as well as of the femur of FIG. 12A, after the removal of the initially installed prosthesis.
Figure 15A:
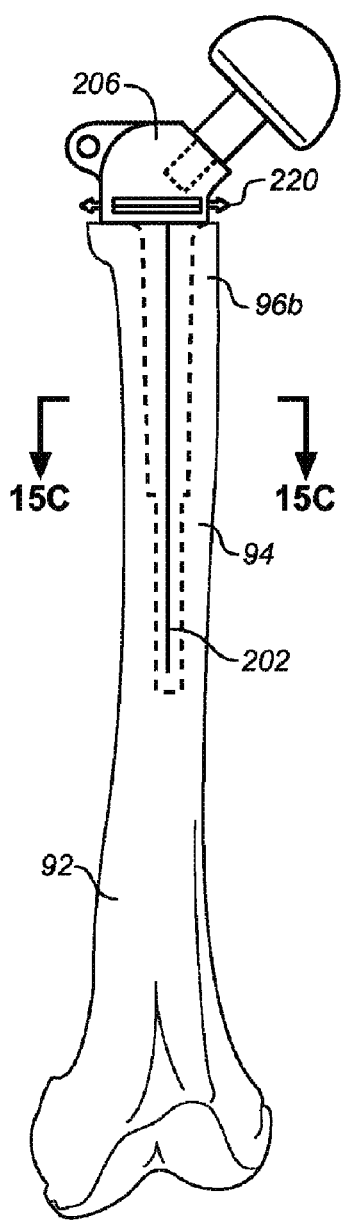
FIG. 15A is a schematic side view in elevation of the femur of FIG. 12A after the bone has reconstituted around the prosthesis and in the shape of the flexible member.
Figure 15B:
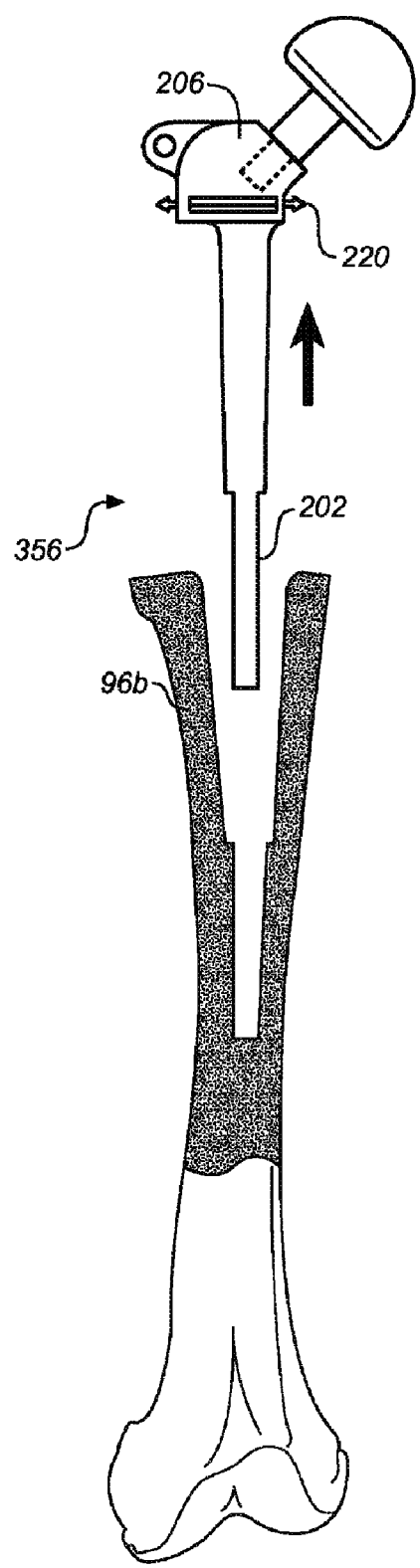
FIG. 15B is a cross-sectional side view in elevation of the femur and prosthesis of FIG. 15A after slicing the bone longitudinally for removal of the prosthesis.

Referring next to FIGS. 13A and 14A-14B, the surgical technique of the present invention utilizes the following apparatus and comprises the following method steps: The initial pre-surgical stage of preparation involves measuring and documenting 300 the damaged or diseased bone. A resection point is determined and a prosthetic device 200 is designed and fabricated 302 in conformity with the patient's needs and the surgical objectives. The device includes an insertable rod 202 that will extend axially and longitudinally into host bone a predetermined length. At decision block 304, a determination is made as to whether a customized bone growth housing 204a, 204b, must be employed. If such a housing is called for, the custom bone growth housing is manufactured prior to surgery 306. If not, the process moves into the surgical phase.

The initial surgical stage of preparation 308 requires the removal of the diseased or damaged area of the bone such that the remaining bone is robust and able to support the new prosthesis. The resection could be required by trauma, such as a severe fracture, or by tumors, multiple previous failed joint replacements, and the like.

The next step is to prepare the bone 310 for acceptance of a prosthesis by cutting the bone perpendicular to the shaft such that a cylindrical tube of robust bone remains at the exposed surface. Continuing the bone preparation step, the residual bone shaft can be expanded by using a cylindrical reamer to size it and shape it to ensure a tight, intimate contact between the femur and the shaft of the prosthesis.

Next the height of the prosthesis above the remaining bone needs is determined 312. There are a variety of strategies to achieve this including the use of preoperative planning, the use of a trial prosthesis and determination of soft tissue tension, the use of a computer navigation system. These techniques are commonly used and straightforward to any surgeon skilled in orthopaedic oncology surgery or joint replacement surgery. Once the desired level of the prosthesis has been established, the length of the bone restoration prosthesis can be decided. The goal for revision hip replacements is to achieve at least 6 to 8 cm of press-fit within the residual tube of bone.

Next, the prosthesis is installed 314 in the host bone. If the femoral prosthesis is to be cemented, cement is placed in the canal and the shaft of the femoral component is inserted and hammered to the desired depth. A cementless process depending on press-fit of the prosthesis into the cortical bone tube may also be employed.

Once the prosthesis has been impacted in the femur (or other bone canal) to the desired depth, the next phase involves the application of the bone growth housing 204a/204b. As noted above, a custom mesh may be prefabricated in the shape of the desired bone using rapid prototype technology and the use of semirigid mesh composed of a variety of polymers including but not limited to polylactic, polyglycolic acids, and collagens. However, a surgical procedure to address a traumatic injury may not afford sufficient time for such prefabrication. Additionally, it may be necessary to remove a portion of the prosthesis, 316, though only temporarily so to facilitate the installation of a bone growth housing.

Next, at decision block 318 the method diverges according to whether a prefabricated custom bone growth housing is to be employed. If not, a bone growth housing is formed 320 in the surgical suite. The bone growth housing (typically mesh) is then passed over the articular portion 206 of the prosthesis circumferentially, thereby enclosing that portion of the prosthesis, and bringing the distal border down 322 and over the residual bone shaft 94. The bone growth housing can be cut at the desired level over the bone shaft such that it overlaps the bone between 1 and 5 cm. The mesh can then be tightened at its distal border over the bone shaft using a band 208, a suture, or a metal wire defining and partially enclosing the cavity space 210 around the prosthesis at the point of the residual bone.

Once installed, the upper part 212 of the semi-rigid bone growth housing used in the proximal femoral version of the invention has an expansion 214 corresponding to the native (resected) greater trochanter. In this region, there is an aperture 216 for attachment of the abductor tendons. The remaining abductor tendons in continuity with the greater trochanter bone and the slightly more distal vastus lateralis tendon can then be passed into the aperture and fixed to the prosthesis 324 directly using wires, bands, sutures and techniques well known in the field of orthopaedic surgery.

At this point the distally enclosed cavitary space 210 is filled 326 with a variety of bone graft substitutes, including but not limited to cancellous bone chips, demineralized bone matrix, bone morphogenic proteins, autologous cancellous bone graft, and/or autologous bone marrow. As the cavitary space is filled, the upper (proximal aspect) 212 of the bone growth housing is attached 328 to the upper aspect of the prosthesis using the triangular rail attachment points 220, sutures, bands 222, or wires such that the entire cavity is now sealed, enclosing the bone graft but allowing the vascular ingrowth and remodeling needed to reconstitute bone. In a preferred embodiment, the upper aspect of the bone growth housing can be formed to include an integral circumferential slot 224 that mates with the rails 220 or other male attachment elements disposed on the prosthesis.

The joint is then reduced 330 into its socket, in the case of hip arthroplasty either as a total hip replacement with an artificial (standard) hip socket or as a partial hip replacement, placing the prosthetic head into the native hip socket. The field is surgery is then closed 332.

The salient difference between the present invention and known prior art resides in the possibility of restoring a new tube or column of bone. As a case example, and referring now to FIG. 13B and FIGS. 15A-16B, if a 15-year-old patient with an osteosarcoma has had a resection and limb salvage surgery using the inventive bone restoration prosthesis, she would gradually remodel the bone grafts within the bone growth housing over the course of 1-2 years to form a new tube of bone 96b. The bone growth housing (e.g., a mesh), in one embodiment, is bioabsorbable, much like absorbable sutures. However, the use of non-absorbable wires is also possible and may be preferred in some instances. Radiographs post surgery would show gradual incorporation of the bone graft into new bone enclosed to the inner shape of the bone growth housing (which would optimally correspond to the actual shape of the femur based on rapid prototyping technology).

Perhaps at 10 years, the patient's prosthesis may undergo failure due to polyethylene wear that gradually leads to loosening of the femoral component (a process called osteolysis). The treatment for this development would include revision of the prosthesis of the femur. In the pre-surgical phase, the existing prosthetic and bone are measured and documented 350. A replacement prosthetic is then selected 352 to conform to the new bone shaft 96b. If the prosthesis is actually loose (which may or may not be the case), it may be able to be easily removed from the new tube of bone. If it is well fixed, the treating surgeon may need to perform an extended trochanteric osteotomy through the newly reconstituted bone to free up the prosthesis 354 by essentially opening up the femur with a plurality of longitudinal slices 98. But by that time the patient would have a completely new tube of bone 96b. (It should be noted that ideally only one transection is dividing the femur into two fragments, rather than the four fragments shown in FIG. 15C.) The originally installed prosthesis is then removed 356. The replacement prosthesis 400 is then installed 358. If slices have been made in the earlier reconstituted bone, the new prosthesis 400 is secured in the bone tube 96b by banding 360 the bone with radially disposed bands 402. ligaments and tendons are attached 362 as necessary and the surgical field is closed 364.

Using the reconstituted bone formed from the methods of the present invention, in a succeeding reconstructive surgery, the patient may potentially be treated with an even shorter or equal length prosthesis placed in the reconstituted femur that was used in the initial reconstructive procedure. This is a significant advancement in the art, in that the new tube is new bone and enables the body to heal with its own tissue rather than with scar tissue.

Method Steps Applicable to Knee Arthroplasty: The steps in the knee are essentially analogous to those described for the hip, above. For the tibial version of the prosthesis, the mesh contains an aperture along the anterior aspect for passage of the patellar tendon and/or tibial tubercle and direct attachment of these structures to the tibial bone restoration prosthesis analogous to that described for the hip abductors above.

Figure 17A:
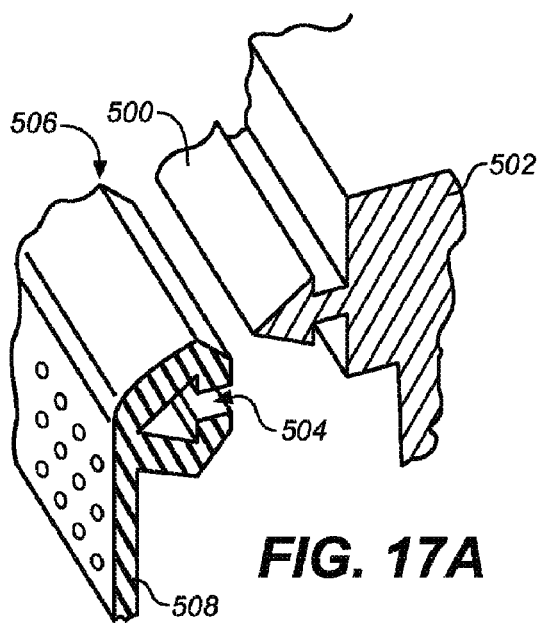
FIG. 17A is an exploded diagrammatic perspective view of the prosthetic of the present invention and a portion of the flexible member or bone growth housing showing a means of connecting the two elements.
Figure 17B:
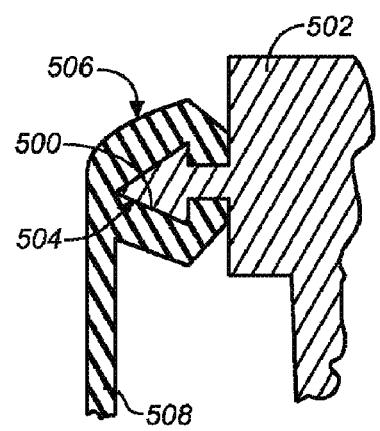
FIG. 17B is a schematic cross-sectional side view in elevation showing the elements of FIG. 17A connected.

Referring finally to FIGS. 17A through 19, there is shown a variety of techniques for attaching the bone growth housing to the prosthesis of the present invention. FIGS. 17A-17B show a first preferred embodiment, comprising rails 500 either integrally formed from or attached to the outer surface of the articular portion of the prosthesis 502. The rails function as a male element that matingly connects with a conforming female slot 504 circumferentially formed in the proximal aspect 506 of the bone growth housing.

Figure 18:
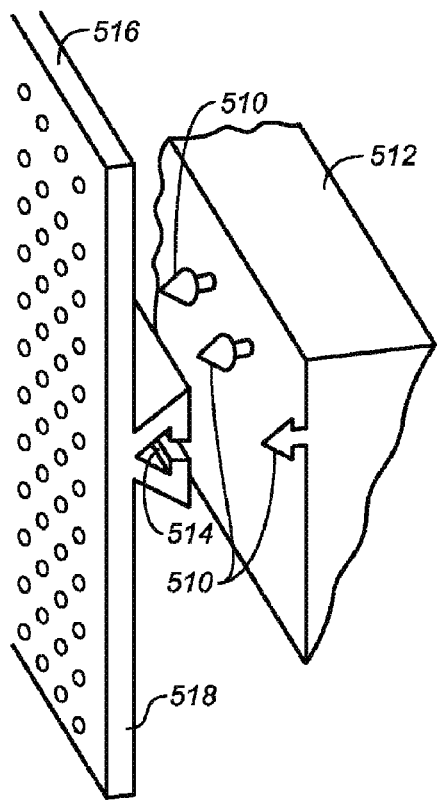
FIG. 18 is an exploded diagrammatic perspective view showing an alternative means of connecting the inventive prosthesis to its flexible member.

FIG. 18 shows a second preferred embodiment of bone growth housing attachment elements, in this instance comprising male points 510 rather than rails, formed in the articular proximal portion of the prosthesis 512 and adapted for matable coupling with a slot 514 formed in the proximal aspect 516 of the bone growth housing 518.

Figure 19:
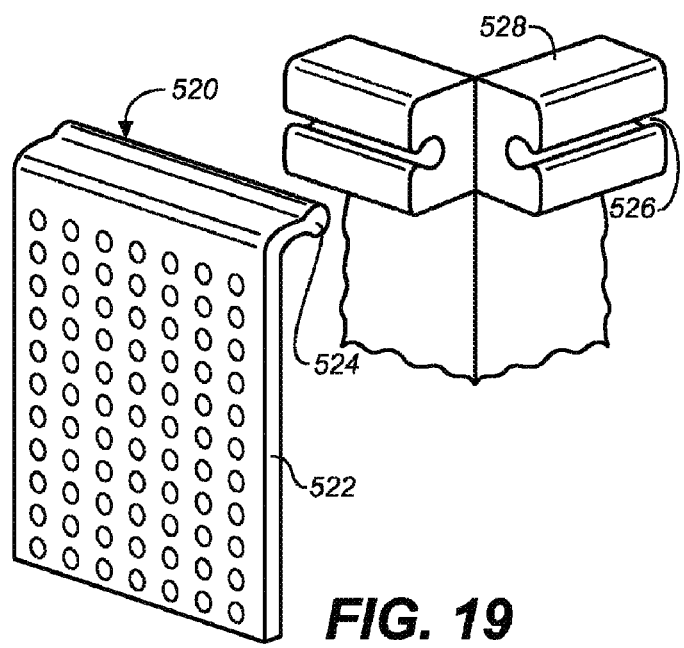
FIG. 19 is an exploded diagrammatic perspective view showing yet another alternative form of connecting the prosthesis to the flexible member.

In a third preferred embodiment of the bone growth housing attachment means, FIG. 19, the proximal aspect 520 of the bone growth housing 522 includes an expansion 524 that snaps into or slidably inserts into a channel 526 formed in the proximal aspect of the prosthesis 528.

In describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

Thus, while the above disclosure is sufficient to enable one of ordinary skill in the art to practice the invention, and provides the best mode of practicing the invention presently contemplated by the inventor, the disclosure of the preferred embodiments of this invention does not limit the invention to the exact construction, dimensional relationships, and operation shown and described. Various modifications, alternative constructions and method steps, changes, and equivalents will readily occur to those skilled in the art and may be employed, as suitable, without departing from the true spirit and scope of the invention. Therefore, the above description and illustrations should not be construed as limiting the scope of the invention, which is defined by the appended claims.

What is claimed as invention is:

1. A method for reconstructing osseous skeletal defects in a femur, said method comprising the steps of:
    (a) measuring and documenting the damaged or diseased femur;
    (b) determining a resection point in said femur;
    (c) designing and fabricating a femoral prosthesis in conformity with the patient's needs and surgical objectives, the femoral prosthesis including an insertable rod that will extend axially and longitudinally into host bone a predetermined depth;
    (d) determining whether to use a customized or prefabricated bone growth housing;
    (e) manufacturing said bone growth housing;
    (f) resecting said damaged or diseased femur by perpendicularly cutting and removing the diseased or damaged area of the femur such that the remaining bone shaft is able to support a new prosthetic apparatus;
    (g) expanding the residual bone shaft as necessary to size and shape it for a tight, intimate contact between the femur and the insertable rod of the prosthesis;
    (h) determining a desired height of the prosthesis above the remaining bone;
    (i) installing the insertable rod of the prosthesis into the residual bone shaft to said predetermined depth;
    (j) installing the bone growth housing;
    (k) wrapping a proximal margin of the bone growth housing over and around an upper, proximal portion of the prosthesis circumferentially, thereby enclosing that portion of the prosthesis, and bringing a distal margin of the bone growth housing down and wrapping said distal margin over and around the residual bone shaft;
    (l) cutting the bone growth housing at the desired level over the residual bone shaft such that it overlaps the bone;
    (m) tightening and attaching the bone growth housing at its distal margin over the residual bone shaft so as to define and enclose a cavitary space around the prosthesis at the point of the residual bone shaft;
    (n) if applicable, passing tendons through an aperture in the bone growth housing and attaching them to the prosthesis;
    (o) filling the cavitary space with osteoconductive and/or inductive materials thereby creating a bed of bone graft material;
    (p) attaching the proximal margin of the bone growth housing to the upper, proximal portion of the prosthesis so as to enclose the entire cavitary space, said cavitary space modeled to substantially match the shape of the removed area of the femur; and
    (q) reducing the joint into its socket;
    wherein said bone growth housing comprises a perforated flexible sheet forming said cavitary space, which cavitary space circumferentially surrounds said prosthesis between said flexible member and said prosthesis; said perforations being between 100 and 2000 micrometers in diameter so as to allow for the ingress of blood vessels during the maturation process of reconstructed bone; and
    wherein the prosthesis is supported by the bed of graft material surrounding it and is gradually unloaded as the bed matures into a new column of solid bone.

2. The method of claim 1, wherein attachment of the proximal margin of the bone growth housing to the upper, proximal portion of the prosthesis is via at least one attachment member, said at least one attachment member is selected from the group consisting of rails, runners, suture holes, and a slot.

3. The method of claim 2, wherein said at least one attachment member comprises rails disposed on the upper, proximal portion of the prosthesis, and wherein said bone growth housing includes a female slot circumferentially formed in said proximal margin for matingly connecting with said rails.

4. The method of claim 2, wherein said at least one attachment member comprises a plurality of male points disposed on the upper, proximal portion of the prosthesis and said bone growth housing includes a female slot circumferentially formed in said proximal margin for matingly connecting with said plurality of male points.

5. The method of claim 2, wherein said articular upper, proximal portion of the prosthesis includes a slot and said bone growth housing includes an expansion circumferentially disposed said proximal margin for insertion into said slot.

6. The method of claim 1, wherein said osteoconductive and/or inductive materials are selected from the group consisting of cancellous bone allograft chips, calcium sulfate, calcium carbonate, calcium phosphate, demineralized bone matrix, bone morphogenic proteins, autologous cancellous bone graft, autologous bone marrow, and any combination thereof.

7. The method of claim 1, wherein said bone growth housing is fabricated from a material selected from the group consisting of metal mesh, demineralized bone matrix, and polymers.

8. The method of claim 7, wherein said bone growth housing is fabricated from a resorbable polymer.

9. The method of claim 8, wherein said resorbable polymer is selected from the group consisting of polylactic acid, polyglycolic acid, collagen, and hyaluronate.

\* \* \* \* \*